US012329488B2

(12) United States Patent
Kretz et al.

(10) Patent No.: US 12,329,488 B2
(45) Date of Patent: *Jun. 17, 2025

(54) GLOVE DISPENSING SYSTEMS AND METHODS THEREOF

(71) Applicant: QWIK GLOVE LLC, Beachwood, OH (US)

(72) Inventors: Paul O. Kretz, North Royalton, OH (US); John M. Kretz, Lodi, OH (US)

(73) Assignee: QWIK GLOVE LLC, Beachwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/975,342

(22) Filed: Dec. 10, 2024

(65) Prior Publication Data

US 2025/0099196 A1    Mar. 27, 2025

Related U.S. Application Data

(63) Continuation of application No. 18/635,123, filed on Apr. 15, 2024, now Pat. No. 12,201,393.

(60) Provisional application No. 63/459,725, filed on Apr. 17, 2023.

(51) Int. Cl.
*A61B 42/40* (2016.01)
*A47G 25/90* (2006.01)
*A61B 42/50* (2016.01)

(52) U.S. Cl.
CPC ............ *A61B 42/40* (2016.02); *A47G 25/904* (2013.01); *A61B 42/50* (2016.02)

(58) Field of Classification Search
CPC ........ A61B 42/40; A61B 42/50; A47G 25/904
See application file for complete search history.

(56) References Cited

U.S. PATENT DOCUMENTS

| | | | |
|---|---|---|---|
| 2004/0149788 A1* | 8/2004 | Sato | A47G 25/904 223/111 |
| 2005/0155133 A1* | 7/2005 | Sato | A61B 42/00 221/45 |
| 2017/0296281 A1* | 10/2017 | Gaines | A47G 25/90 |
| 2019/0159619 A1* | 5/2019 | Burk | A47G 25/904 |

* cited by examiner

*Primary Examiner* — Nathan E Durham
(74) *Attorney, Agent, or Firm* — Frost Brown Todd LLP

(57) ABSTRACT

A disposable glove apparatus. A cartridge of disposable gloves can be configured and mounted for presentation to a user. A user's hands in proximity to an open portion of a glove causes a gas flow to inflate a pair of gloves. A user can insert hands into the open gloves and remove them, thereby donning gloves in an easy and sanitary manner.

20 Claims, 10 Drawing Sheets

GLOVE DISPENSING SYSTEMS AND METHODS THEREOF

CROSS-REFERENCE TO RELATED APPLICATIONS

This application is a continuation of U.S. Ser. No. 18/635,123, filed Apr. 15, 2024, entitled GLOVE DISPENSING SYSTEMS AND METHODS THEREOF, which claims the benefit of U.S. Ser. No. 63/459,725, filed Apr. 17, 2023, entitled GLOVE DISPENSING SYSTEMS AND METHODS THEREOF, the disclosures of which are incorporate herein in their entirety.

BACKGROUND

Disposable gloves are gloves worn for a specific purpose and then thrown away. Disposable gloves help keep germs and infection from spreading to you and to the other person. Disposable gloves are regularly worn in care and medical environments to prevent the spread of infection. Disposable gloves are also worn by those involved with food preparation and serving. In general, disposable gloves find use by those in retail, industrial and commercial environments where the sanitary handling of food, chemicals, medical goods and other materials is important.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
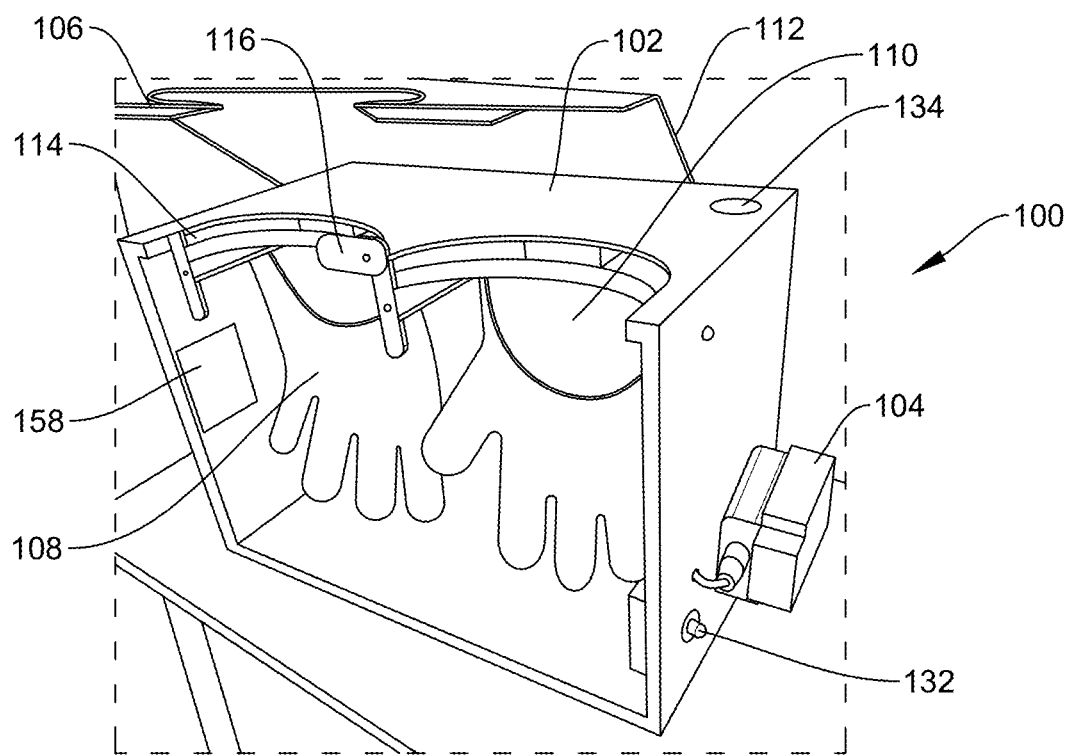
FIG. 1 is a perspective view of an example glove dispensing apparatus of the present disclosure.

Various non-limiting embodiments of the present disclosure will now be described to provide an overall understanding of the principles of the structure, function, and use of the systems and methods disclosed. One or more examples of these non-limiting embodiments are illustrated in the selected examples disclosed and described in detail with reference made to the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems and methods disclosed herein are described in detail by way of examples and with reference to the figures. The examples discussed herein are examples only and are provided to assist in the explanation of the systems and methods described herein. None of the features or components shown in the drawings or discussed below should be taken as mandatory for any specific implementation of any of these the systems or methods unless specifically designated as mandatory. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible.

It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The systems and methods disclosed herein generally relate to the dispensing of disposable gloves. In accordance with various embodiments, the gloves can be suitably arranged as a stack in a hanging configuration. In an embodiment, both a left and right handed glove can be presented for dispensing. In an embodiment, the disposable gloves can be made of plastic, including nitrile, vinyl, latex, polyethylene, paper, wax-coated paper, bees-wax coated paper, or any other suitable material, including biodegradable plastics such as polylactic acid (PLA), polyhydroxyalkanoates (PHA), or starch-based plastics, recycled materials, or a variety of other materials that may be environmentally friendly or sustainably sourced.

Figure 2:
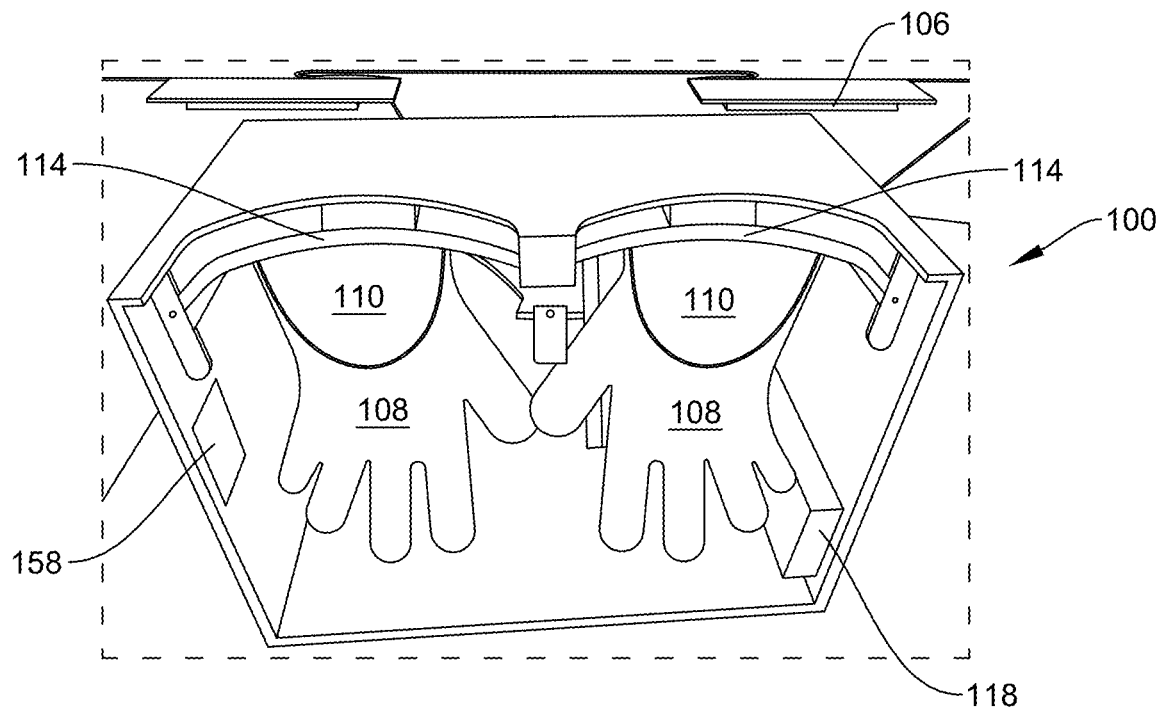
FIG. 2 is a front view of an example glove dispensing apparatus of the present disclosure.

Referring now to FIGS. 1-2 there is shown an example embodiment of a disposable glove dispensing apparatus 100 that can be utilized in a system and method for disbursing disposable gloves. The glove dispensing apparatus 100 includes a housing 102 which can include a bottom, sides, a back, a top, and other suitable structure for providing a substantially unit for disbursing disposable gloves. The unit can be self-contained and be provided as a counter-top device, or as a wall-mounting device.

In the embodiment shown, the housing 102 can have a generally open front portion in which the disposable gloves are presented for use. Representative sizes and dimensions for a housing of the type depicted in FIGS. 1-2 are shown in the diagrams of FIGS. 12-15. The housing shown can be modified dimensionally as desired for application-specific purposes.

Mounted to the housing in an operational configuration are various components useful for the system and method of providing disposable gloves to a user in a relatively convenient and sanitary manner. A power supply 104 can supply any electrical power requirements. The power supply 104 can be suitably configured to utilize, or convert, line voltage, such as 120 VAC to suitable power requirements for powered components such as lighting and gas inflation devices. The power supply can convert AC line voltage to DC voltage. The power supply can also be a replaceable and/or a rechargeable battery. The power supply can include a battery mount for insertion and removal of a lithium ion battery, for example. The power supply can be mounted anywhere on, off, or near the glove dispensing apparatus 100 and provide suitable electrical power to the various powered components. A counter 158 can be mounted in or on the housing 102 to provide a count of gloves mounted in a stacked configuration, as described below. The counter 158 can be wired or wirelessly connected to an indicator such as a light source or a computer device, such as a Smartphone. The counter 158 can provide a total count, and can be configured to signal a low count. A low level sensor 134 can indicate a predetermined low level of glove supply. The low level sensor 134 can be visual, audible, or signal to a remote device. The low level sensor 134 can be wired or wirelessly connected to an indicator such as a light source, sound source, or a computer device, such as a Smartphone.

A plurality of gloves 108 can be provided in a stacked configuration that can be referred to as a cartridge of gloves, as depicted in more detail in FIGS. 9-13 In general, gloves have a front side and a back side. The front side, which is the palm side, faces the user and is configured such that an entry portion 110 of each glove 108 for a user's hands is presented to the front of the housing 102. In an embodiment, gloves 108 can be stacked in a hanging arrangement from an upper glove holder 114, as discussed in detail below. In general, a right and a left hand glove 108 can be presented simultaneously. However, in an embodiment, only one of a right or left hand glove can be presented.

Lighting 106 can be suitably positioned for use to illuminate the area in which a user's hands enter the gloves. Lighting 106 can be mounted on a lighting panel 112 that can be configured to also function as a splash guard. Lighting 106 can be any suitable type, including LED lighting.

In some embodiments, the glove dispensing apparatus 100 may be equipped with a sterilization system to sanitize the gloves 108, either before being dispensed or subsequent to being donned by a user. The sterilization system can be integrated into the glove dispensing apparatus 100 in various ways. In some embodiments, the lighting 106 is either augmented by, or replaced by, ultraviolet (UV) light sources, such as UV-C LEDs or UV lamps, which are known to have germicidal properties. The UV light can be positioned to irradiate the gloves 108 just before, during, or immediately after dispensing. Additionally, or alternatively, a sanitizing mist or spray system can be used that applies a fine mist of a sanitizing agent, such as hydrogen peroxide, alcohol, or other suitable disinfectants, to the gloves 108 and/or the user's hands prior to or during dispensing. The sterilization system can be activated automatically upon gloves 108 dispensing or be user-controlled via an interface on the machine.

Gloves 108 can be inflated for relatively easy and sanitary insertion of the user's hands. In an embodiment inflation is caused by a flow of gas, such as air, directed into the entry portion 110 of each glove 108. As can be appreciated, for each of the left and right gloves, the entry portion 110 faces the user, that is, the entry portion for both the left and right gloves is on the palm side of the gloves. Air can be provided from any suitable source, including an air compressor, a tank of compressed air, or a blower that moves ambient air. The air can be directed to the entry portion 110 of each glove 108 by one or more tubes, nozzles, fittings, or other suitable fluid-flow components, as discussed below. In use, therefore, a user can put on gloves from the dispenser without ever touching the outside of the gloves. By not touching the outside of the gloves during donning, the chance of contamination from the user to the outside of the gloves is eliminated. In some embodiments, an air stream is also directed towards the user's hands as the user is inserting their hands into the gloves. This air stream can aid in drying the user's hands, which can increase the ease with which the user dons the gloves. This air stream can be sourced from the same suitable source supplying air into the entry portion 110 of the glove 108 or from a separate source.

Once a user's hands are inserted into the gloves 108 in a general downward motion to guide the fingers and thumb into the glove. Once the user's hands are inserted into the gloves the user can draw his/her hands away from the device to remove the gloves 108 from the device. In an embodiment, removal can be accomplished by tearing the gloves away from predetermined frangible portions thereof. In some embodiments, with the gloves 108 mounted in the glove dispensing apparatus 100 in a side-by-side arrangement in various embodiments, a user can place each of their hands into a respective glove 108 simultaneously and then tear both gloves away in a single motion.

The present disclosure is not limited to a side-by-side arrangement of gloves, as various glove arrangements can be employed within the scope of the invention. In some embodiments, the gloves may be oriented in a stacked configuration, with gloves for left hands and right hands alternating within the stack. This stacked arrangement allows a user to place their hands in a stacked formation and then insert them into the gloves simultaneously. The stacked glove configuration can provide the advantage of a more compact form factor for the glove dispensing apparatus as compared to a side-by-side arrangement. Furthermore, while many of the described embodiments depict gloves hanging in a vertical orientation, alternative embodiments may include gloves stored horizontally in a stacked arrangement within the glove dispensing apparatus. In such embodiments, two horizontal stacks of gloves can be positioned side-by-side, with one stack containing gloves oriented for the left hand and the other stack containing gloves oriented for the right hand. To facilitate donning, an air stream can be directed into the entry portion of the top glove on each horizontal stack, causing the gloves to inflate and allowing the user to simultaneously don both left and right gloves.

In an embodiment, the system of the glove dispensing apparatus 100 can operate by the following method. The glove dispensing apparatus 100 is positioned to be conveniently accessed by a user and powered by line voltage or battery power. As a user approaches various sensors can be actuated. A first sensor can detect the proximity of a user's hands and actuate the lighting 106, if necessary. A second sensor can detect the proximity of a user's hands and actuate the gas inflation to cause inflation of the gloves 108. A third sensor can detect the position of the outermost glove and adjust the stack of gloves, if necessary. Thus, in a method of use, a user approaches the glove dispensing apparatus 100, extends his/her hands near the stack of gloves 108, upon inflation of the gloves 108, the user puts his/her hands into the inflated gloves. The user then draws back his/her hands to remove the gloves 108 from the stack.

In an embodiment, as shown in FIGS. 3-6, a proximity sensor 116 that can also function as an LED holder can be mounted in a suitably operational position. In cooperation with the power supply 104, a buck converter and sensor board or other electronics can be housed in an electronics unit 118. Suitable switches for operation, such an on/off switch 132 can be positioned in convenient to use locations. A blower 120 can direct gas through ductwork 122 toward a location generally positioned to direct air into the entry portion 110 of gloves 108. In an embodiment, as shown in the elevation view of FIG. 5, and the plan view (viewing upwardly relative to FIG. 5), ductwork 122 can be generally tubular tubes 128 and fittings and/or rectangular ductwork 126 and fittings, though which the gas can flow through gas nozzles 130 mounted in the upper glove holders 114 and directed toward gloves 108. The blower 120 can be a 12V blower or any suitable blower or air compressor. The moving and/or pressurized gas can be directed by gas nozzles 130 downwardly (as oriented in FIGS. 1-2) in the direction of the entry portion 110 of each glove 108. As the gas, e.g., air, is forced into the glove 108, the glove 108 inflates, thereby providing for unobstructed entry of a user's hands.

Figure 3:
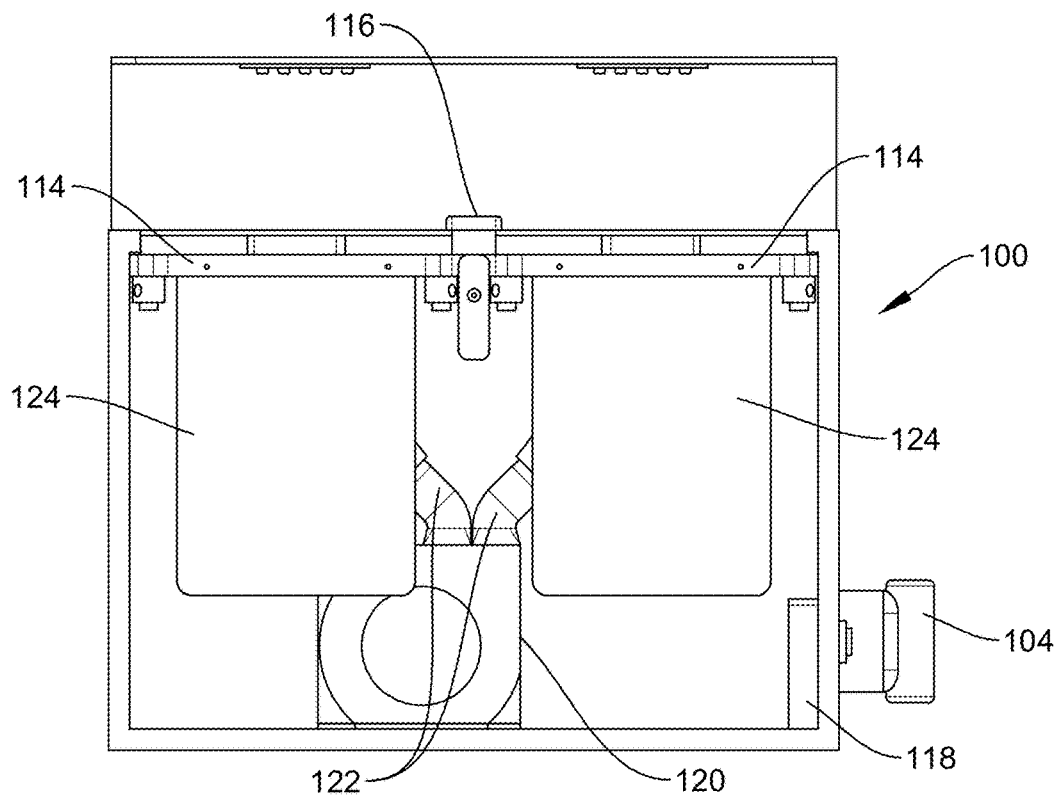
FIG. 3 is a front schematic view of an example glove dispensing apparatus of the present disclosure.
Figure 4:
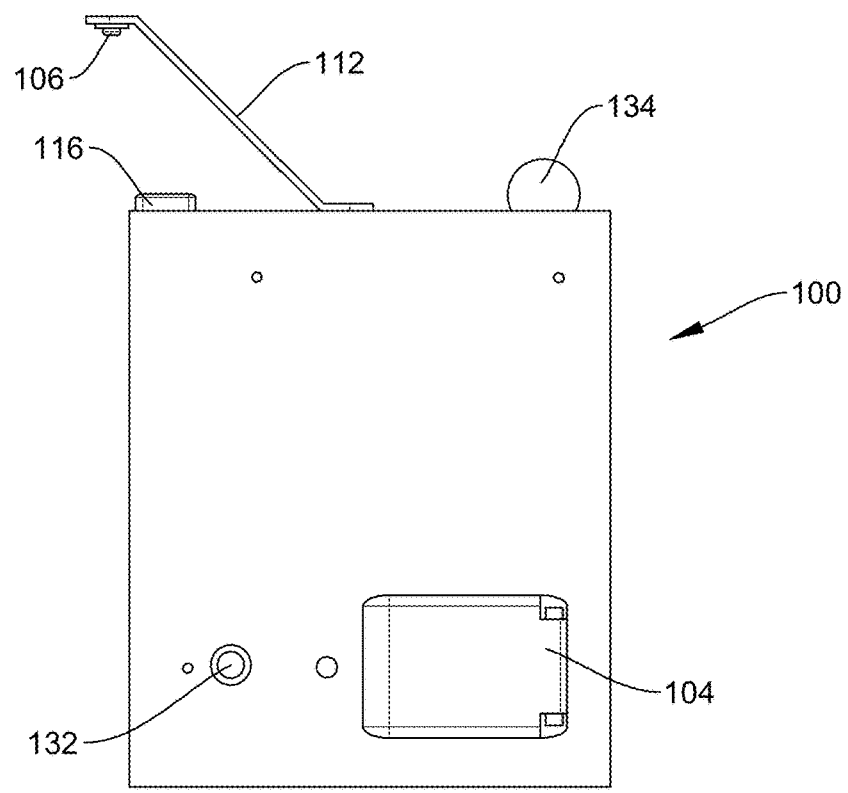
FIG. 4 is a side schematic view of an example glove dispensing apparatus of the present disclosure.
Figure 5:
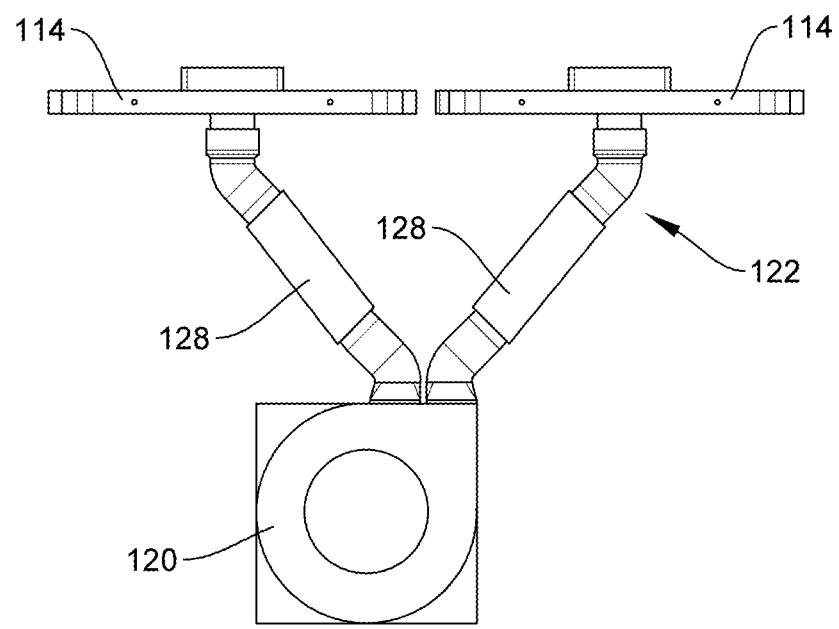
FIG. 5 is a schematic depiction of a representative gas flow system of the present disclosure.
Figure 6:
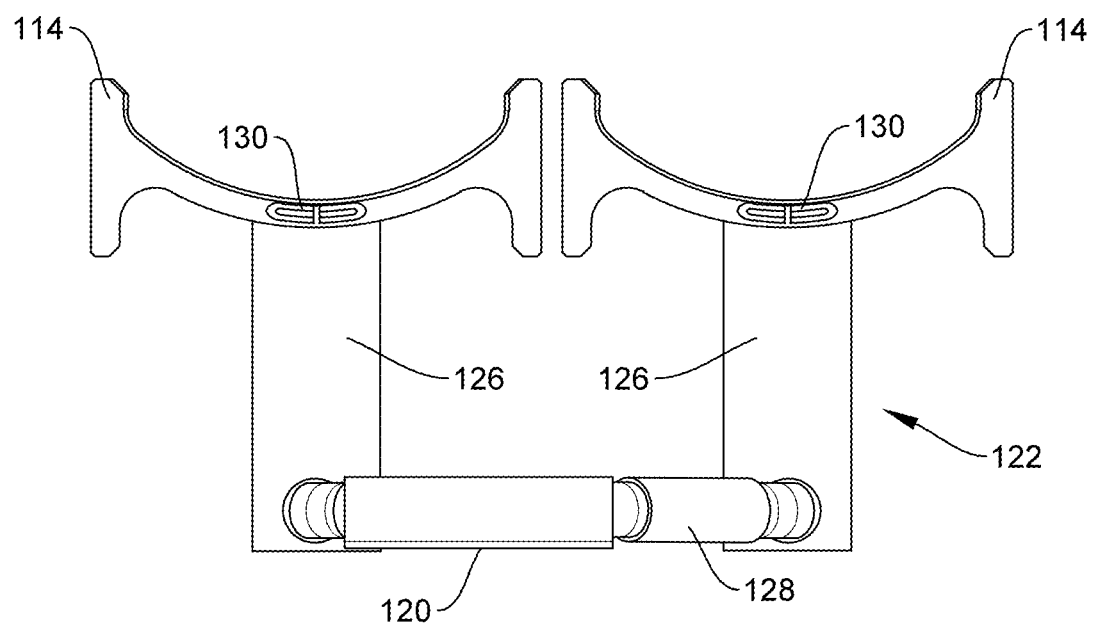
FIG. 6 is a schematic depiction of a representative gas flow system of the present disclosure.
Figure 7:
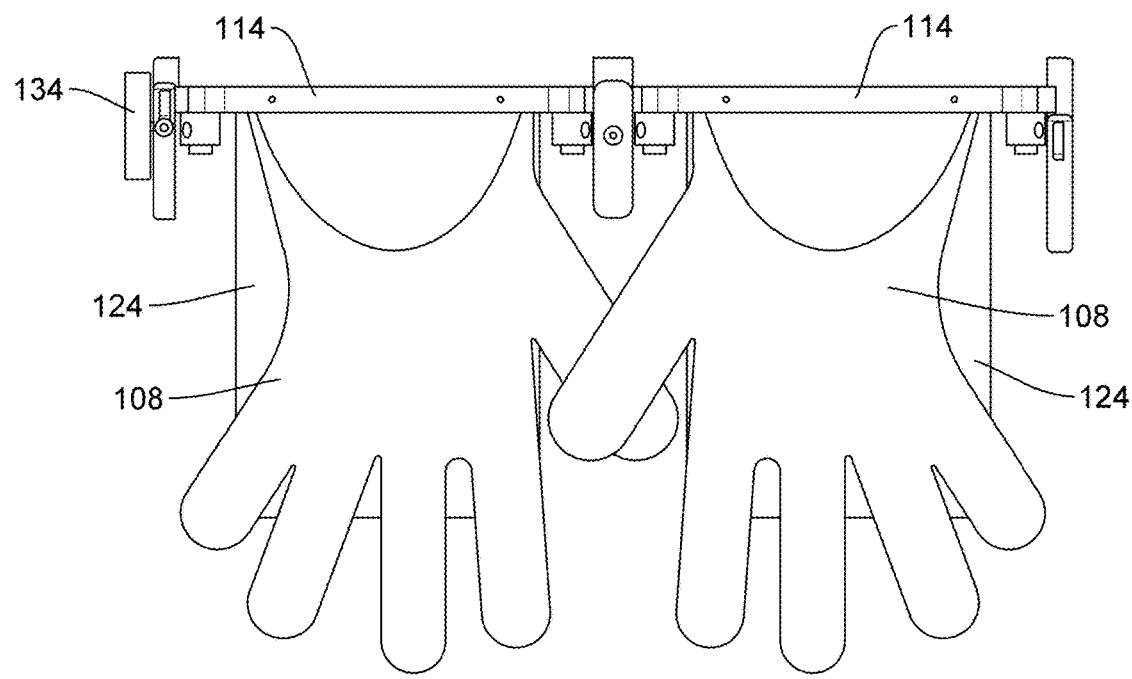
FIG. 7 is a schematic depiction of a representative glove mounting system of the present disclosure.
Figure 8:
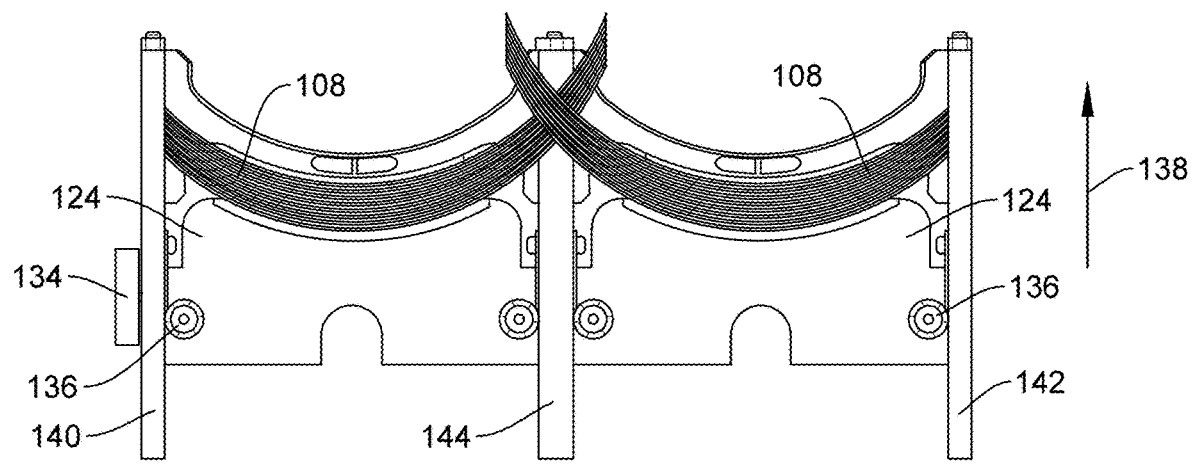
FIG. 8 is a schematic depiction of a representative glove mounting system of the present disclosure.
Figures 9, 10:
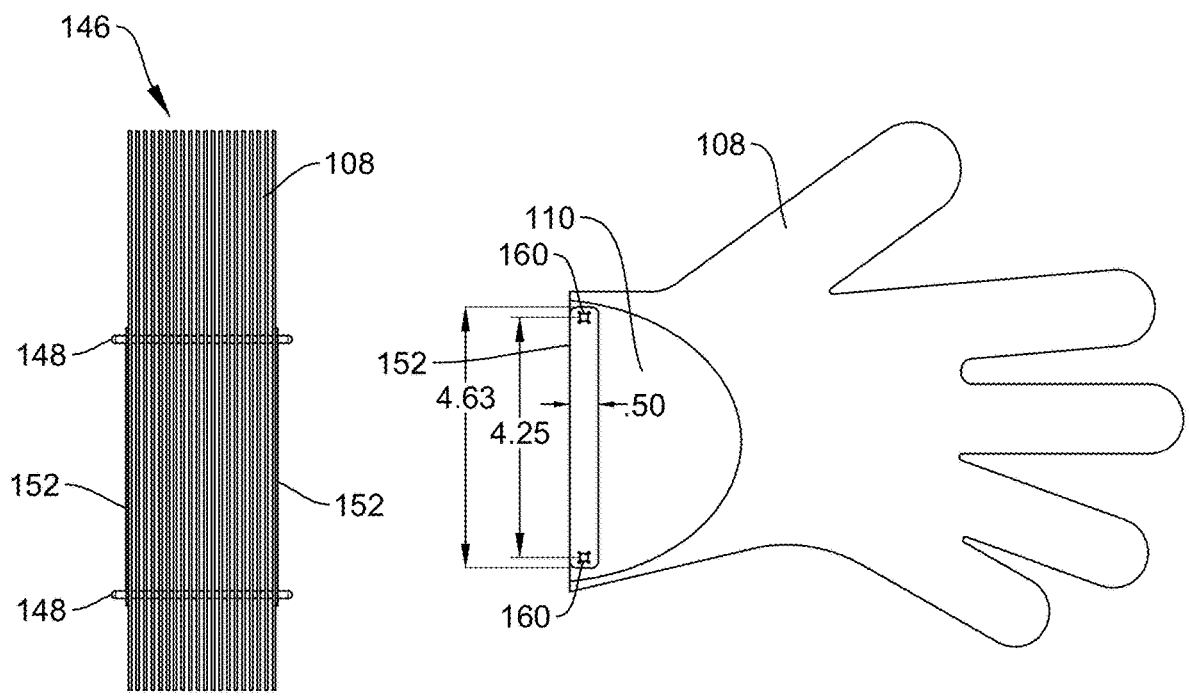
FIG. 9 is a top view of a representative glove cartridge of the present disclosure.
FIG. 10 is a plan view of a representative glove cartridge of the present disclosure.
Figure 11:
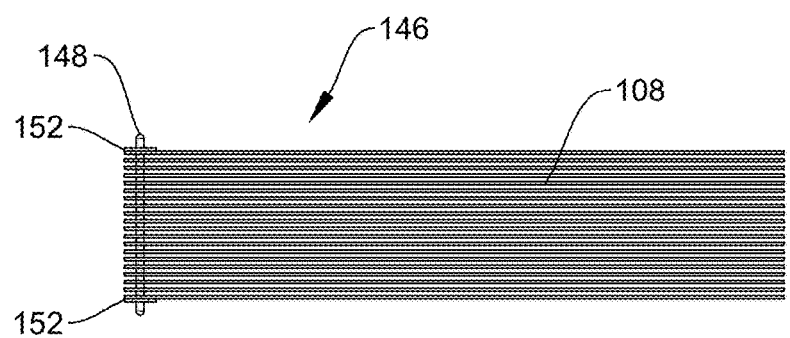
FIG. 11 is a side view of a representative glove cartridge of the present disclosure.

Referring now to FIGS. 3 and 7-8, there is shown representative views of the glove dispensing apparatus 100 showing representative components for managing a stack of gloves 108. A bottom glove panel 124 can be positioned and configured to provide for substantially rigid support of the stack of gloves 108 when operationally positioned as a cartridge of gloves, as depicted in FIG. 7. The bottom glove panel 124 can be slidably mounted onto generally horizontal top rails, such as left side (looking into the front of the glove dispensing apparatus 100) 140, right side rail 142 and center rail 144, as depicted in FIGS. 7-8. As gloves are removed by a user, springs 136 can urge the bottom glove panel toward the front of the glove dispensing apparatus 100, as indicated by arrow 138. The springs 136 can be constant force springs and can be sized and configured as desired for operational use.

Figure 12:
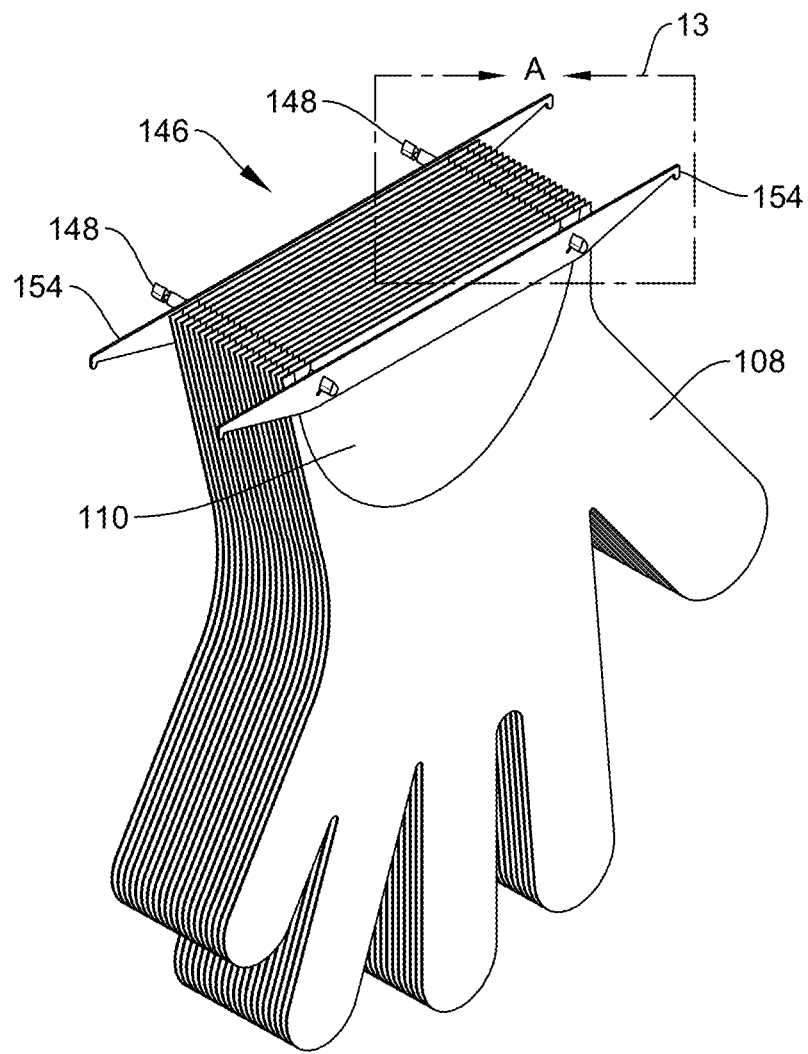
FIG. 12 is a perspective view of a representative glove cartridge of the present disclosure.
Figure 13:
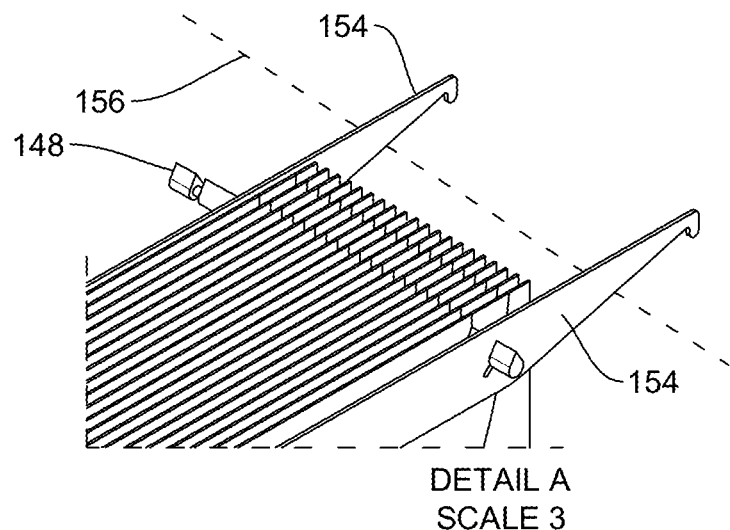
FIG. 13 is a detail view of detail 13 in FIG. 12.

Referring now to FIGS. 9-13, there is shown a representative glove 108 configurations, including a representative glove cartridge 146 configurations. In general, a stack of gloves 108 can be mounted on a pair of parallel rods 148 from which they can be removed. Compression brackets 152 can be affixed on the rods 148 to hold the glove stack into a compact glove cartridge 146. Referring to FIGS. 12 and 13 there is shown one representative configuration of a glove cartridge 146. As shown mounting brackets 154 can be joined to the glove cartridge 146 and extend laterally to rest moveably on one of the support rails, such as right side rail as indicated by the dashed line 156.

Figure 14:
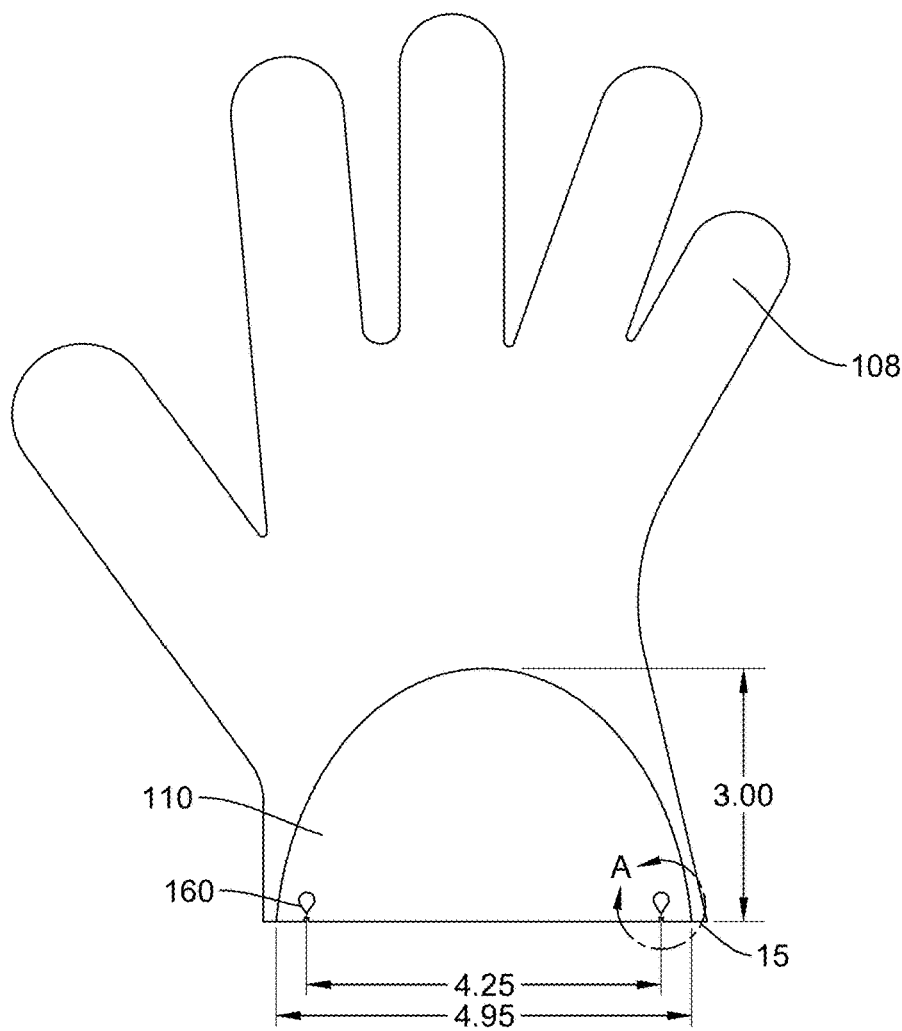
FIG. 14 is a representative depiction of a glove of the present disclosure.
Figure 15:
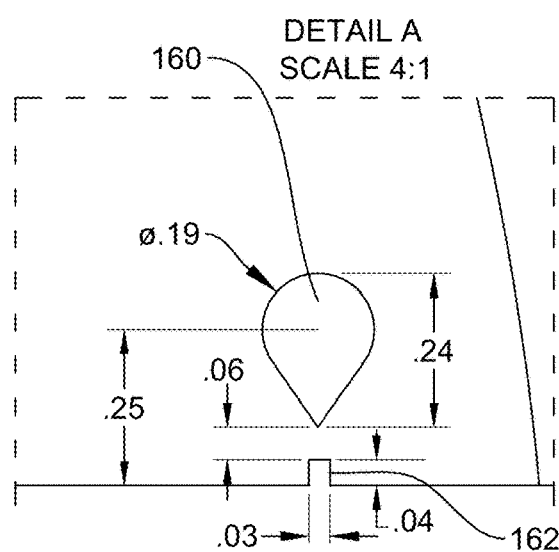
FIG. 15 is a detail view of detail 15 in FIG. 14.
Figure 16:
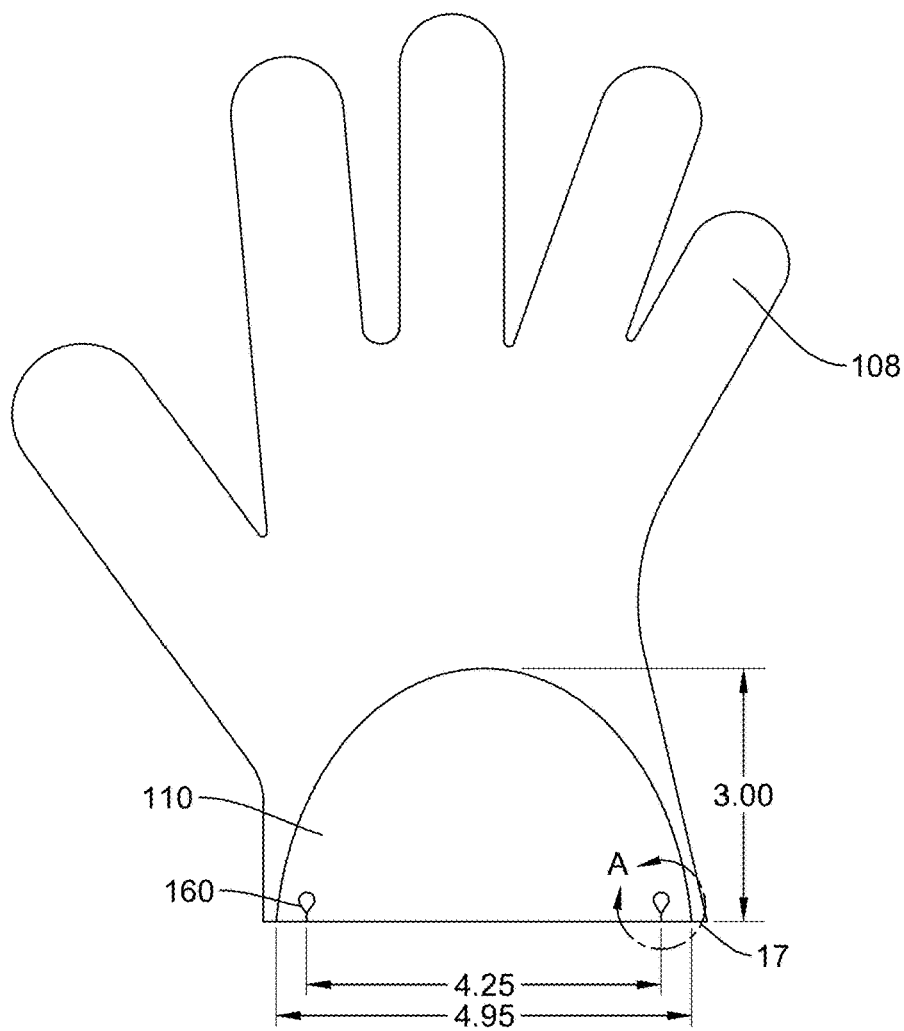
FIG. 16 is a representative depiction of a glove of the present disclosure.
Figure 17:
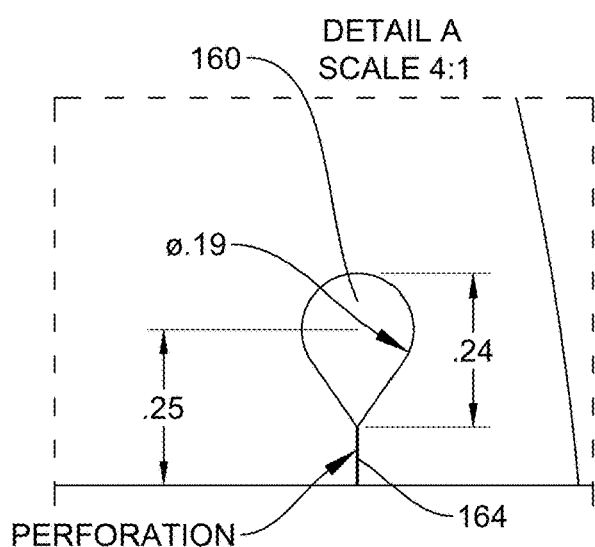
FIG. 17 is a detail view of detail 17 in FIG. 16.
Figure 18:
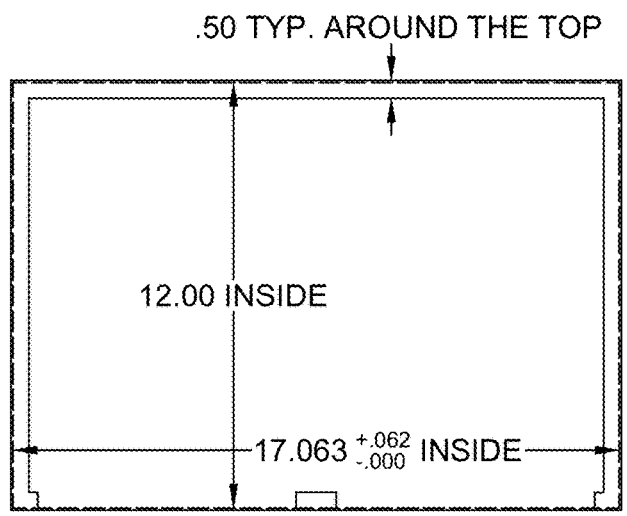
FIGS. 18-21 show representative dimensions for an apparatus of the present disclosure.
Figure 19:
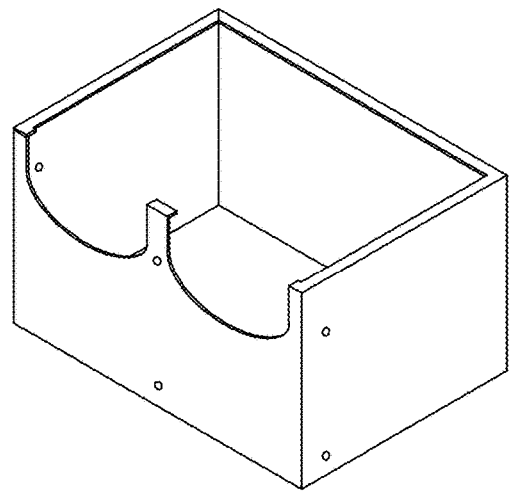
Figure 20:
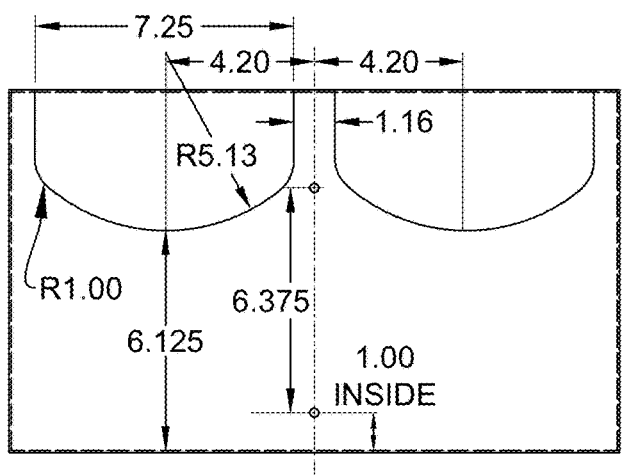
Figure 21:
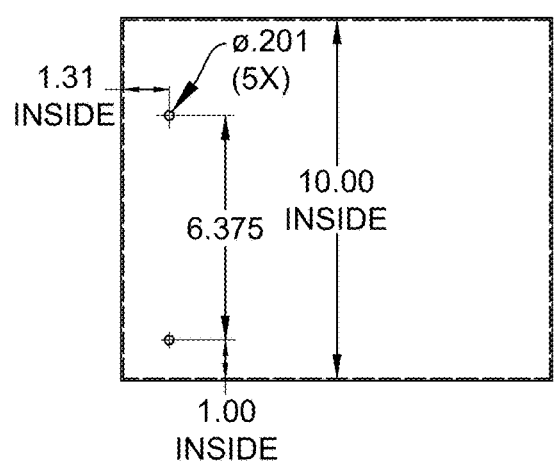
Figure 22:
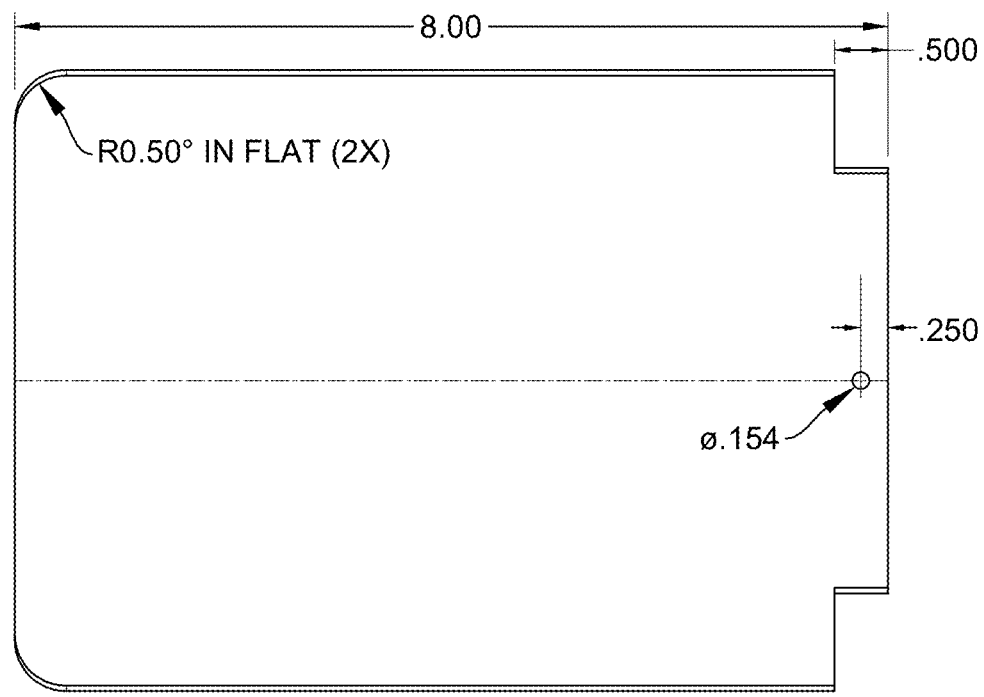
FIGS. 22-23 show representative dimensions for bottom glove panel of the present disclosure.
Figure 23:
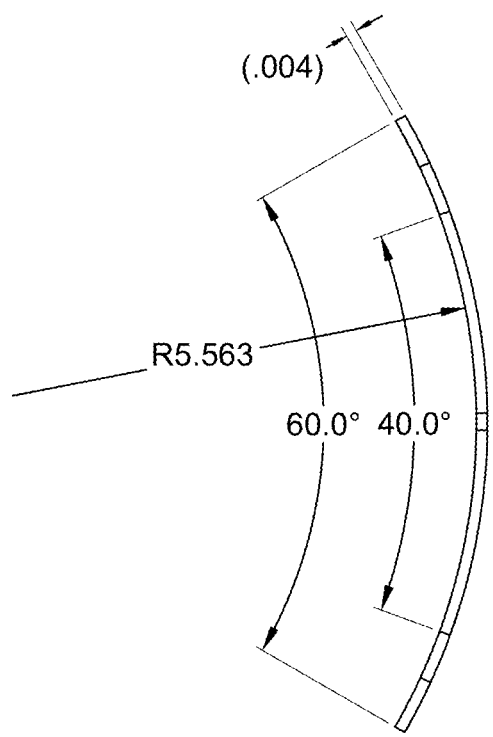

Continuing to refer to FIGS. 9-13 and referring to FIGS. 14-17, representative configurations of a glove 108 are depicted. Apertures 160 (as depicted, e.g., in FIGS. 14-17) can receive the rods 148. Apertures 160 can be any suitable size and shape, including tear-drop shaped, as indicated in one embodiment in detail 15 of FIG. 15 and detail 17 of FIG. 17. To aid in removing gloves 108 from the rods 148 the apertures can be configured as frangible portions for easy tearing. In an embodiment, as shown in FIGS. 14 and 15 a notch 162 can be at a top edge of glove 108 and in the proximity of the aperture 160. The notch 162 can create a stress point at which the glove can frangibly tear. Likewise, as shown in FIGS. 16 and 17 a perforation 164 can be at a top edge of glove 108 and in the proximity of the aperture 160. The perforation 164 can create a stress point at which the glove can frangibly tear. In general, the entry portion 110 on the front gauntlet portion of gloves 108 can be a generally semi-circle, parabolic, arched, or other shape providing sufficient opening for air flow to enter into gloves 108.

In some embodiments, the glove dispensing apparatus 100 can include a counting mechanism configured to keep track of the number of gloves 108 dispensed. The counting mechanism can be operatively connected to a display located on the apparatus itself, for example, which visually indicates the total count of gloves dispensed. This feature can allow users and managers to easily monitor glove usage directly on the glove dispensing apparatus 100. In accordance with another embodiment, the glove dispensing apparatus 100 can further comprise a real-time clock in addition to the counting mechanism. The real-time clock can enable the glove dispensing apparatus 100 to track the number of gloves dispensed within predefined time frames, such as a business day, a specific shift, or other period of time. At the end of the predefined period, the glove dispensing apparatus 100 can communicate the total number of gloves 108 dispensed during that time frame to a designated recipient, such as an owner or manager of the establishment where the glove dispensing apparatus 100 is located. The communication of the glove usage data can be achieved through various means, including but not limited to sending a text message, an email, or transmitting the data to a cloud-based application. This communicated information can allow, for example, the owner or manager to compare the glove usage data with other relevant data, such as the number of sandwiches sold or other types of transactions during the same period, enabling them to determine compliance with hygiene protocols or other predetermined standards.

These and other embodiments of the systems and methods can be used as would be recognized by those skilled in the art. The above descriptions of various systems and methods are intended to illustrate specific examples and describe certain ways of making and using the systems disclosed and described here. These descriptions are neither intended to be nor should be taken as an exhaustive list of the possible ways in which these systems can be made and used. A number of modifications, including substitutions of systems between or among examples and variations among combinations can be made. Those modifications and variations should be apparent to those of ordinary skill in this area after having read this disclosure.

What is claimed is:

1. A glove dispensing apparatus, comprising:
a housing;
a sanitizing system, wherein the sanitizing system stores a sanitizing agent;
a plurality of disposable gloves, wherein each of the plurality of disposable gloves defines an entry portion, wherein the plurality of disposable gloves is arranged into a first cartridge and a second cartridge;
a first glove holder coupled to the housing, wherein the first glove holder comprises a first gas nozzle, wherein the first cartridge is mounted to the first glove holder, wherein the first gas nozzle is externally positioned relative to each of the plurality of disposable gloves of the first cartridge, wherein the first gas nozzle is stationary with respect to the housing;
a second glove holder coupled to the housing, wherein the second glove holder comprises a second gas nozzle, wherein the second cartridge is mounted to the second glove holder, wherein the second gas nozzle is externally positioned relative to each of the plurality of disposable gloves of the second cartridge, wherein the second gas nozzle is stationary with respect to the housing; and
a gas source, the gas source in fluid communication with the first gas nozzle and the second gas nozzle, wherein upon activation of the gas source, a gas is externally delivered into the entry portion of at least one of the plurality of disposable gloves.

2. The glove dispensing apparatus of claim 1, wherein the gas source is any of a blower and a tank of compressed air.

3. The glove dispensing apparatus of claim 1, wherein the gas is delivered simultaneously into two of the plurality of disposable gloves through the first gas nozzle and the second gas nozzle.

4. The glove dispensing apparatus of claim 1, wherein each of the plurality of disposable gloves defines a first and second aperture positioned proximate to a top edge of the disposable glove.

5. The glove dispensing apparatus of claim 4, wherein the first glove holder comprises a first rod and a second rod, wherein for each of the plurality of disposable gloves arranged in the first glove holder, the first rod extends through the first aperture and the second rod extends through the second aperture, wherein the second glove holder comprises a first rod and a second rod, wherein for each of the plurality of disposable gloves arranged in the second glove holder, and wherein the first rod extends through the first aperture and the second rod extends through the second aperture.

6. The glove dispensing apparatus of claim 5, wherein each of the plurality of disposable gloves defines a first perforation extending from the first aperture to the top edge of the disposable glove and a second perforation extending from the second aperture to the top edge of the disposable glove.

7. The glove dispensing apparatus of claim 1, wherein the sanitizing agent comprises alcohol.

8. The glove dispensing apparatus of claim 1, further comprising a sensor, wherein the sensor generates a signal in response to the proximity of a hand of a user.

9. The glove dispensing apparatus of claim 8, wherein responsive to the signal generated by the sensor, the gas source is activated to deliver the gas into the entry portion of at least one of the plurality of disposable gloves.

10. The glove dispensing apparatus of claim 8, wherein responsive to the signal generated by the sensor, the sanitizing system is activated to dispense the sanitizing agent.

11. The glove dispensing apparatus of claim 10, wherein the sanitizing agent is dispensed as a fine mist.

12. A glove dispensing apparatus, comprising:
a housing;
a first stack comprising a plurality of disposable gloves, wherein the first stack is hanging from a first glove holder coupled to the housing;
a second stack comprising a plurality of disposable gloves, wherein the second stack is hanging from a second glove holder coupled to the housing;
at least one ultraviolet light source, wherein the at least one ultraviolet light source is configured to irradiate at least one of the plurality of disposable gloves of the first stack and at least one of the plurality of disposable gloves of the second stack;
a gas source;
a first gas nozzle in fluid communication with the gas source, the first gas nozzle externally positioned proximate to the first stack;
a second gas nozzle in fluid communication with the gas source, the second gas nozzle externally positioned proximate to the second stack; and
wherein the gas source is configured to deliver a gas through the first gas nozzle to inflate one of the plurality of disposable gloves of the first stack and deliver the gas through the second gas nozzle to inflate one of the plurality of disposable gloves of the second stack, and wherein the first gas nozzle and the second gas nozzle are each stationary with respect to the housing.

13. The glove dispensing apparatus of claim 12, further comprising a sensor, wherein the sensor generates a signal in response to the proximity of a hand of a user.

14. The glove dispensing apparatus of claim 13, wherein responsive to the signal generated by the sensor, the at least one ultraviolet light source is activated.

15. A glove dispensing apparatus, comprising:
a housing;
a dispensable sanitizing agent;
a first plurality of disposable gloves hanging from a first glove holder, wherein the first plurality of disposable gloves includes a first front glove and a first back glove, wherein the first glove holder is coupled to the housing;
a second plurality of disposable gloves hanging from a second glove holder, wherein the second plurality of disposable gloves includes a second front glove and a second back glove, wherein the second glove holder is coupled to the housing, wherein the second plurality of disposable gloves are laterally spaced and parallel to the first plurality of disposable gloves, wherein each of the first plurality of disposable gloves and the second plurality of disposable gloves defines an entry portion;
at least one ultraviolet light source, wherein the at least one ultraviolet light source is configured to irradiate at least the first front glove and the second front glove;
a first nozzle positioned externally proximate to the first front glove, wherein the first nozzle is stationary with respect to the housing;
a second nozzle positioned externally proximate to the second front glove, wherein the second nozzle is stationary with respect to the housing;
a gas source in fluid communication with each of the first nozzle and the second nozzle; and wherein the gas source is configured to inflate the first front glove and the second front glove by directing a gas into the respective entry portions.

16. The glove dispensing apparatus of claim 15, wherein the first glove holder comprises a spring coupled to a first back glove panel and the second glove holder comprises a spring coupled to a second back glove panel, wherein the first back glove panel delivers a force to the first back glove and the second back glove panel delivers a force to the second back glove.

17. The glove dispensing apparatus of claim 15, further comprising at least one sensor.

18. The glove dispensing apparatus of claim 17, wherein the at least one sensor comprises any of a proximity sensor and a low level sensor.

19. The glove dispensing apparatus of claim 17, wherein responsive to the signal generated by the at least one sensor, the at least one ultraviolet light source is activated and the sanitizing agent is dispensed.

20. The glove dispensing apparatus of claim 15, wherein the gas source comprises any of a tank of compressed air, a blower, and an air compressor.

\* \* \* \* \*